(12) United States Patent
Jeong (10) Patent No.: US 7,365,837 B2
(45) Date of Patent: Apr. 29, 2008

(54) VISION INSPECTION APPARATUS USING A FULL REFLECTION MIRROR

(75) Inventor: Joon-Young Jeong, Seoul (KR)

(73) Assignee: Mirtec Co., Ltd. (KR)

( * ) Notice: Subject to any disclaimer, the term of this patent is extended or adjusted under 35 U.S.C. 154(b) by 268 days.

(21) Appl. No.: 10/529,953

(22) PCT Filed: Sep. 29, 2003

(86) PCT No.: PCT/KR03/01982

§ 371 (c)(1),
(2), (4) Date: Jan. 20, 2006

(87) PCT Pub. No.: WO2004/032592

PCT Pub. Date: Apr. 15, 2004

(65) Prior Publication Data

US 2006/0132759 A1  Jun. 22, 2006

(30) Foreign Application Priority Data

Oct. 1, 2002  (KR) .................. 10-2002-0059966
Sep. 25, 2003 (KR) .................. 10-2003-0066656

(51) Int. Cl.
*G01N 21/00* (2006.01)
(52) U.S. Cl. ............... 356/237.5; 356/237.1; 356/237.4
(58) Field of Classification Search ........... 356/300, 356/399–401
See application file for complete search history.

(56) References Cited

U.S. PATENT DOCUMENTS 4,152,723 A * 5/1979 McMahon et al. .......... 348/126

(Continued)

FOREIGN PATENT DOCUMENTS

JP    59137803    8/1984

(Continued)

OTHER PUBLICATIONS

European Office Action, EPP92177, dated Jul. 2, 2007 All references cited in the Office action and not previously submitted are listed above.

(Continued)

*Primary Examiner*—Layla G. Lauchman
*Assistant Examiner*—Jerreas Underwood
(74) *Attorney, Agent, or Firm*—Cantor Colburn LLP (57) ABSTRACT

The present invention relates to a vision inspection apparatus and method using total reflection mirrors. The present invention provides a vision inspection apparatus using the total reflection mirrors comprising; a board position control module for fixing a printed circuit board; an independent lighting unit for primarily illuminating the printed circuit board; a photographing position control module for changing a reflection angle to required location coordinates of the printed circuit board; a camera for obtaining an image of the printed circuit board; a control unit including a motion controller, a lighting controller, and an to image processor to control the components; and a vision processing unit for reading the image obtained through the camera and judging whether the image is good or bad. The present invention has effects capable of obtaining a clear image of inspection objects by increasing a quantity of light entered into the camera through a stationary direct illuminating type of independent lighting unit, and accomplishing a precise inspection by preventing shadows from generating on the vision inspection of the object such as a printed circuit board on which different sizes of components are mounted.

6 Claims, 11 Drawing Sheets

U.S. PATENT DOCUMENTS

| | | | | |
|---|---|---|---|---|
| 4,277,175 | A | * | 7/1981 | Karasaki et al. ............. 356/394 |
| 5,105,149 | A | * | 4/1992 | Tokura ....................... 324/752 |
| 5,489,985 | A | | 2/1996 | Mochida et al. ............ 356/398 |
| 5,561,696 | A | * | 10/1996 | Adams et al. ................. 378/58 |
| 5,621,811 | A | * | 4/1997 | Roder et al. ................ 382/147 |
| 5,898,492 | A | * | 4/1999 | Imaino et al. ........... 356/237.1 |
| 6,043,876 | A | * | 3/2000 | Holliday et al. ......... 356/237.1 |
| 6,249,598 | B1 | * | 6/2001 | Honda et al. ............... 382/150 |

FOREIGN PATENT DOCUMENTS

| | | |
|---|---|---|
| JP | 01295140 | 11/1989 |
| JP | 08247736 | 9/1996 |
| KR | 2001-0017027 | 3/2001 |
| KR | 1020010017027 | 3/2001 |

OTHER PUBLICATIONS

The State Intellectual Property Offic of P.R. China; Application No. 038236540; Dec. 22, 2006 All the references cited in the Search Report are listed above.

PCT International Search Report; International application No. PCT/KR03/01982; International filing date: Sep. 29, 2003, Date of Mailing: Nov. 27, 2003.

* cited by examiner

VISION INSPECTION APPARATUS USING A FULL REFLECTION MIRROR

TECHNICAL FIELD

The present invention relates to a vision inspection apparatus and method using total reflection mirrors.

BACKGROUND ART

Generally, a surface mounting technology (SMT) for assembling surface mounting devices (SMD) on a printed circuit board (PCB) etc. comprises a technology of miniaturizing and integrating the surface mounting devices, and technologies of developing precise assembly equipment for assembling the surface mounting devices precisely and operating various kinds of assembly equipments.

In this connection, a surface mounting assembly line is consisted of apparatuses such as a surface mounting machine and a vision inspection apparatus, wherein the surface mounting machine, for mounting the surface mounting devices on the printed circuit board, is supplied various kinds of the surface mounting devices supplied in forms such as tape, stick and tray from a feeder and transfers to a mounting position on the printed circuit board, then, locates the devices on a predeterminate position on the printed circuit board, and the vision inspection apparatus inspects whether mounted states for the devices are good or bad before and after the completion of soldering process of the devices, and transfers the printed circuit board to the next process depending upon results obtained through the vision inspection apparatus.

At this time, a vision inspection method using a conventional vision inspection apparatus adjusts an initial position at a position adjusting apparatus when the printed circuit board that the soldering process is completed is transferred through a conveyor, and inspects whether the mounted states are good or bad by photographing soldering positions of various kinds of devices with a camera and outputting illuminating states of the soldering positions at the vision inspection apparatus to a monitor and calculating them when a lighting is illuminated on the printed circuit board after the completion of the adjustment.

However, the prior art vision inspection apparatus and method have problems that each component accompanies large loads on its driving and serious vibrations on its halt since the camera is fixed and the printed circuit board is moved, or the printed circuit board is fixed and the camera is moved for photographing various soldering parts on the printed circuit board, thereby separating the devices from the original position by a vibration of the inspection apparatus itself when the mounted state of the devices is inspected before the soldering process. Further, a wide installation space is required due to a large-scale of the apparatus itself since a movable space of the camera and the printed circuit board should be occupied. In addition, the prior art has a problem that an inspection position cannot visually confirmed during the test since a distance between the camera and an inspection object is close.

On the other hand, Korean Registered Patent No. 340012 has proposed "Object inspection method and computer vision system using a movable mirror".

Figure 1:
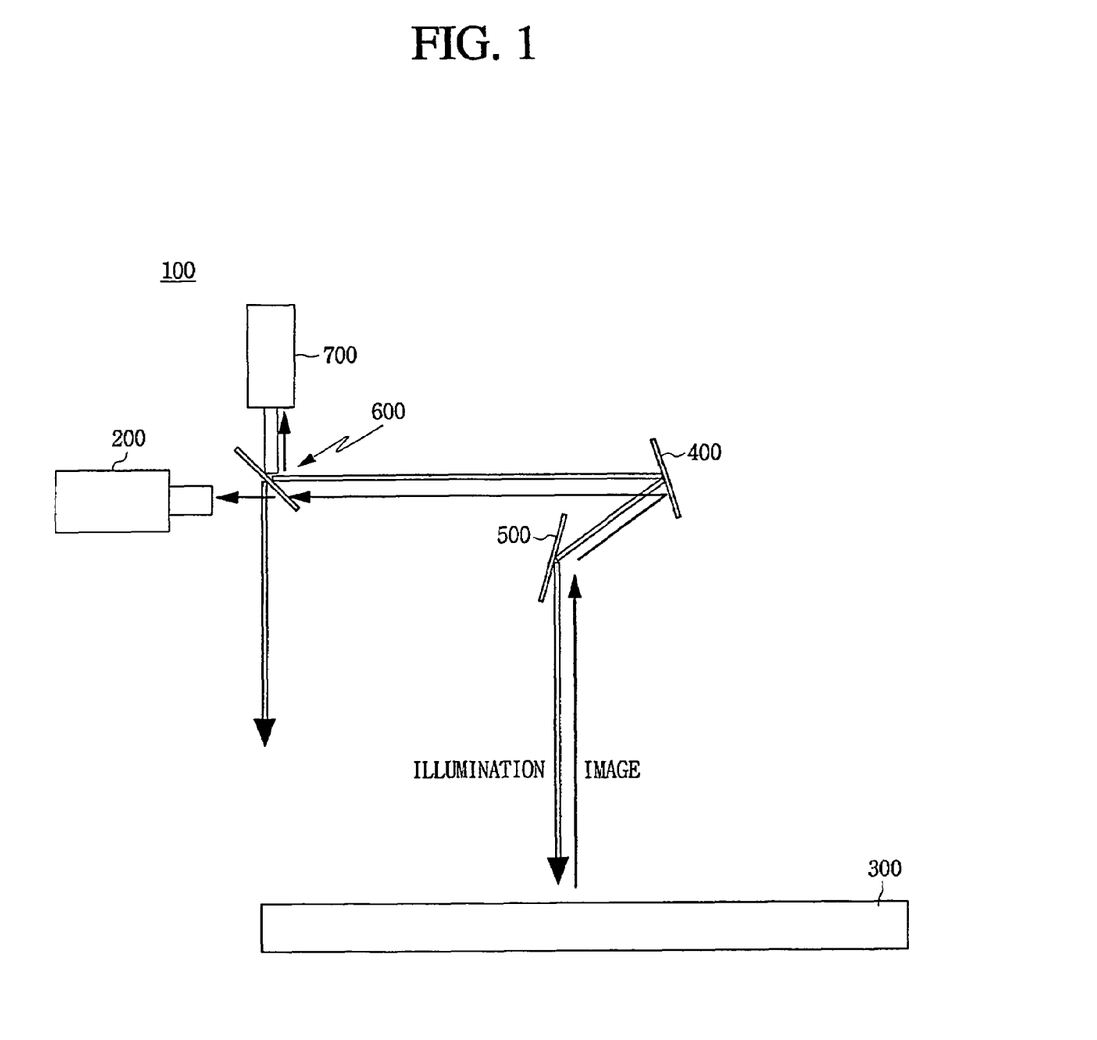
FIG. 1 is an overall structural view for illustrating the prior registered invention.
Figure 2:
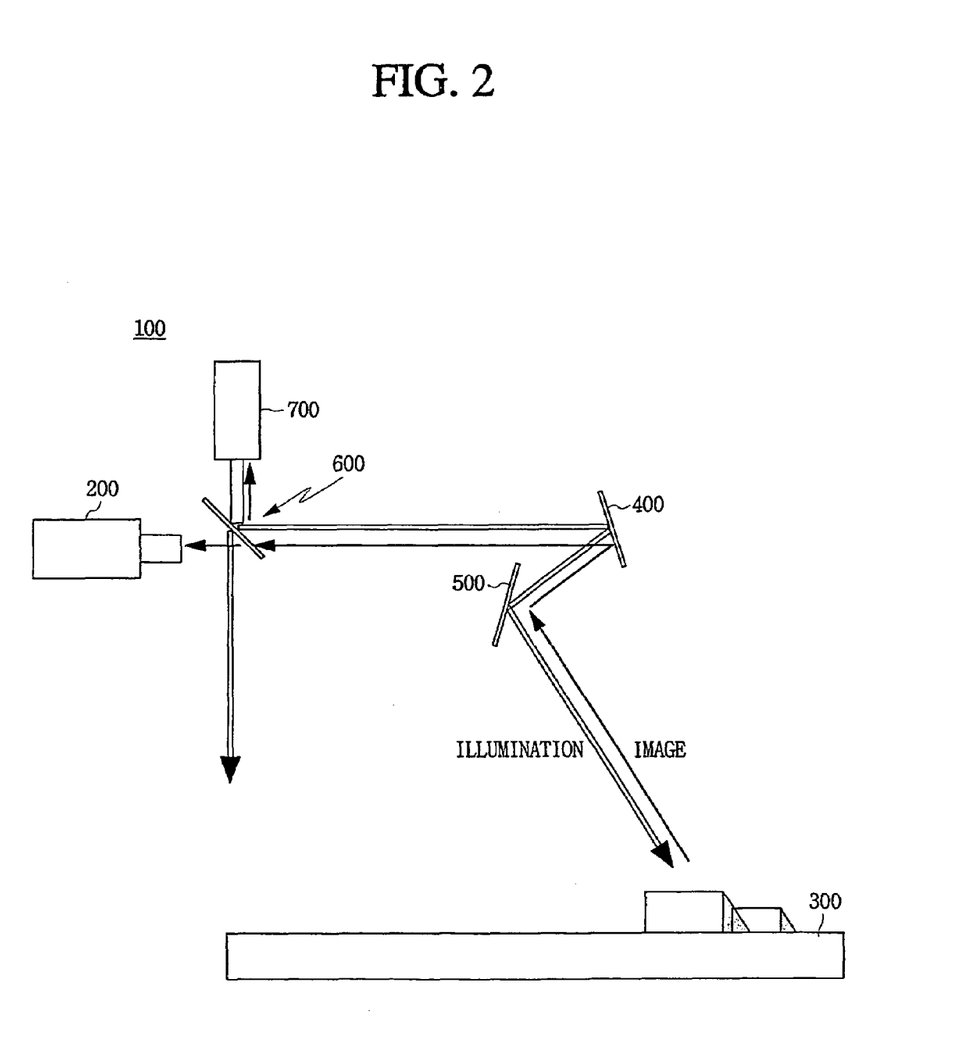
FIG. 2 is a structural view for illustrating an operating state of the prior registered invention.

FIG. 1 is an overall structural view for illustrating the prior registered invention, and FIG. 2 is a structural view for illustrating an operating state of the prior registered invention.

Referring to FIG. 1, X-Y axis movable mirrors 400 and 500 driven by a high-speed motor, a half mirror 600, and a light source 700 are installed between an inspection area 300 and a camera 200. Therefore, the vision system captures images about small areas in the inspection area 300 and operates the movable mirrors 400 and 500 with a high speed to obtain an image of the entire area, thereby accomplishing an inspection. The vision system 100 of the prior registered invention makes a mechanical movable portion extremely small to increase an inspection speed and vary a light path by using the movable mirror, thereby excluding a mechanical mechanism and minimizing an occurring of noises and shocks.

However, the above-mentioned prior registered invention has a problem as follows.

First, since a distance between the inspection area 300 and the light source 700 is distant, losses of a quantity of light transmitted from the light source 700 to the inspection area 300 and a quantity of light transmitted from the inspection area 300 to the camera 200 become lager in proportion to a square of the distance between the inspection area 300 and the light source 700. That is, brightness of the images transmitted to the camera 200 decreases in inverse proportion to a square of the distance. Especially, the half mirror 600 installed on a light path in order to coincide an image path with an illumination path can not accomplish a precise inspection since the image of the inspection area 300 can not be transmitted clearly to the camera 200 as a quantity of light of the illumination or the image passed through due to its characteristics is lost about a half.

Second, as shown in FIG. 2, light finally illuminated to the inspection area 300 becomes inclined light rather than vertical light as a method of changing a path of light by using the X-Y axis movable mirrors 400 and 500 is employed. While the inclined light has no problem when an object in the inspection area 300 is formed in a plane, when the printed circuit board on which various components having different heights are mounted is inspected, reliability of the inspection is reduced since a clear image can not be obtained due to shadows generated by the each component.

DISCLOSURE OF INVENTION

Therefore, a primary object of the present invention to provide a vision inspection apparatus and method using total reflection mirrors capable of expecting an improving effect of inspection operation efficiency as not only a modifying operation of a photographing position is promptly performed but also a driving torque and a vibration are minimized by changing the photographing position by rotating an X-axis total reflection mirror and an Y-axis total reflection mirror.

In addition, it is another object of the present invention to provide a vision inspection apparatus and method using total reflection mirrors provided with a stationary direct illuminating type of illumination and capable of obtaining a clear image of inspection objects by increasing a quantity of light entered into a camera.

Further, it is still another object of the present invention to provide a vision inspection apparatus and method using total reflection mirrors capable of accomplishing a precise inspection by employing a direct illuminating method to the inspection object to prevent shadows from generating on the inspection of the object such as a printed circuit board on which different sizes of components are mounted.

To accomplish the above-mentioned objects, the present invention provides a vision inspection apparatus using total reflection mirrors comprising; a board position control module for fixing a printed circuit board, on which components are mounted, on a suitable inspection position; an independent lighting unit installed at a just upper part of the board position control module and provided with a primary lighting for primarily illuminating the printed circuit board; a photographing position control module, installed at a just upper part of the independent lighting unit, for changing a reflection angle by attaching the total reflection mirrors on axes of X-Y axis motors to required location coordinates on the printed circuit board; a camera for obtaining images of the printed circuit board reflected from the photographing position control module; a control unit including a motion controller for controlling the photographing position control module and the board position control module, a lighting controller for controlling an operation of the independent lighting unit, and an image processor for controlling an operation of the camera and converting the image entered to the camera into digital data; and a vision processing unit for reading the image obtained through the camera and judging whether the image is good or bad.

Further, the present invention provides a vision inspection method using total reflection mirrors comprising the steps of: fixing a printed circuit board on a suitable inspection position through a board position control module; illuminating the printed circuit board with an independent lighting unit; adjusting an incidence angle and a reflection angle with the total reflection mirrors attached on axes of X-Y axis motors in order to transmit an image of the printed circuit board to the camera; converting the image entered to the camera into digital data; and reading the image obtained through the camera and judging whether mounted components are good or bad.

BRIEF DESCRIPTION OF THE DRAWINGS

These and other features, aspects, and advantages of preferred embodiments of the present invention will be more fully described in the following detailed description, taken accompanying drawings. In the drawings.

BEST MODE FOR CARRYING OUT THE INVENTION

Hereinafter, the detailed description of a preferred embodiment of the present invention will be apparent in connection with the accompanying drawings.

Figure 3A:
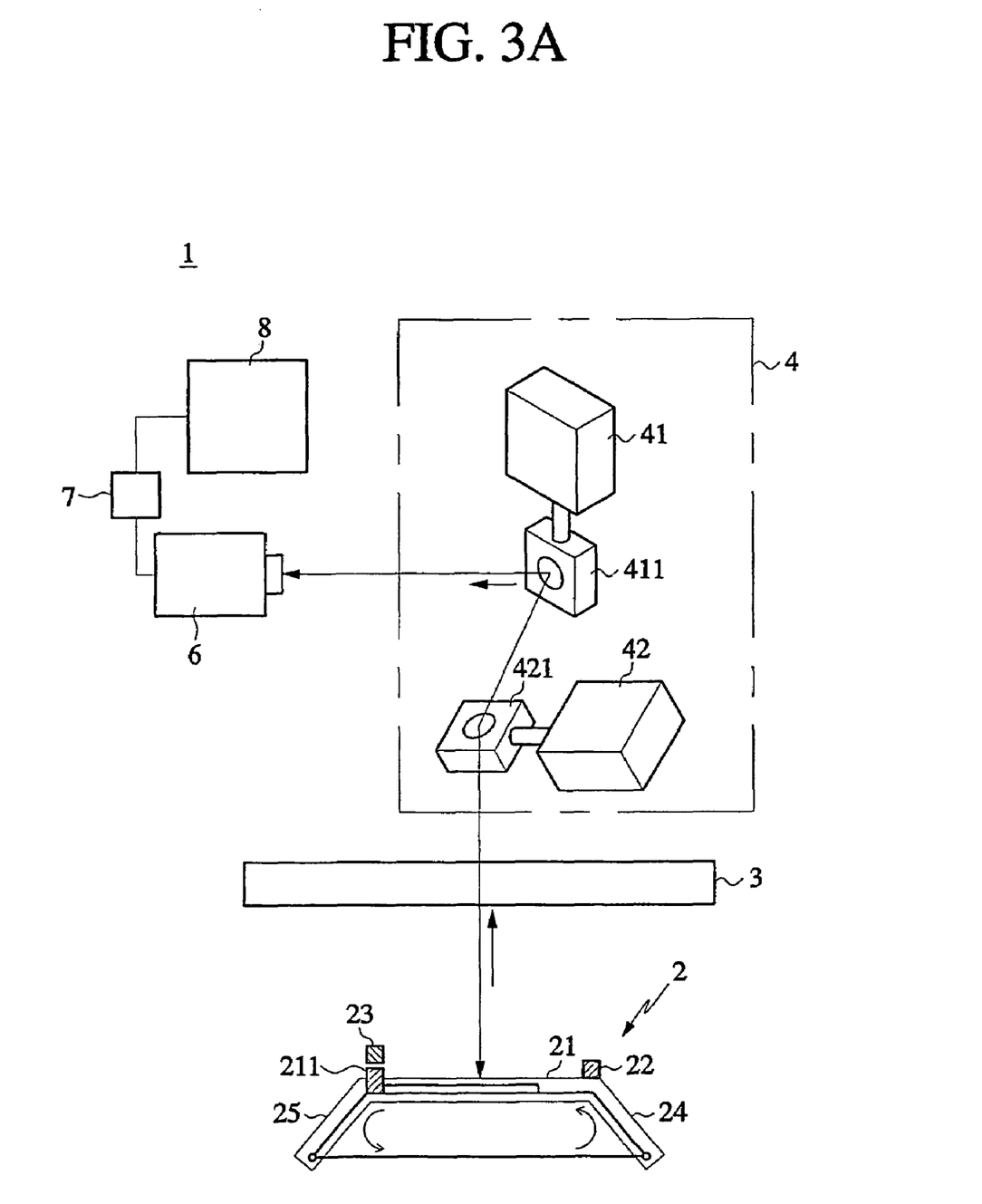
FIG. 3A is a schematic view for illustrating an overall structure of a vision inspection apparatus using total reflection mirrors in accordance with the present invention.

Referring to FIG. 3A, a vision inspection apparatus 1 in accordance with the present invention is installed so that a printed circuit board that a surface mounting operation is completed in a surface mounting assembly line can accomplish a vision inspection prior to a movement to the next process through a conveyor of a preceding apparatus. As a preferred embodiment, the vision inspection apparatus is installed between a surface mounting machine provided with a conveyor and a re-flow machine or between a high-speed mounting machine and a heteromorphy-mounting machine in the surface mounting assembly line. The vision inspection apparatus in the prior art surface mounting assembly line does not need to change its location as the vision inspection apparatus is located at a dead-space formed between conveyors of the preceding/following apparatuses, and may be used in a stand-alone table type without any connection with the preceding/following apparatuses.

On the other hand, a board position control module 2, for controlling a moving of the printed circuit board between the preceding/following apparatuses, is a conveyor structure for fixing the printed circuit board moving along the conveyor of the preceding apparatus on a suitable inspection position; as shown in FIG. 3A, provided with a board fixture 21 located at a higher location than the conveyors of the preceding/following apparatus by forming inclined slopes 24 and 25 at its one end and the other end. The board fixture 21 is provided with first and second detecting sensors 22 and 23 for detecting a flow and a position of the printed circuit board and a stopper 211 for forcefully stopping the printed circuit board by detected values of the sensors 22 and 23.

As described above, the first detecting sensor 22, closely installed at the one end slope 24 of the board fixture 21, accomplishes functions that not only detects the flow of the printed circuit board transferred from the preceding apparatus and stops the conveyor of the preceding apparatus but also operates the stopper 211 installed on the board fixture 21. And, the second detecting sensor 23 accomplishes a function that the printed circuit board to be tested is supplied from the preceding apparatus by detecting whether the tested printed circuit board is transferred to the following apparatus. Therefore, the printed circuit board to be tested at the board position control module 2 is prepared (S1).

Figure 4:
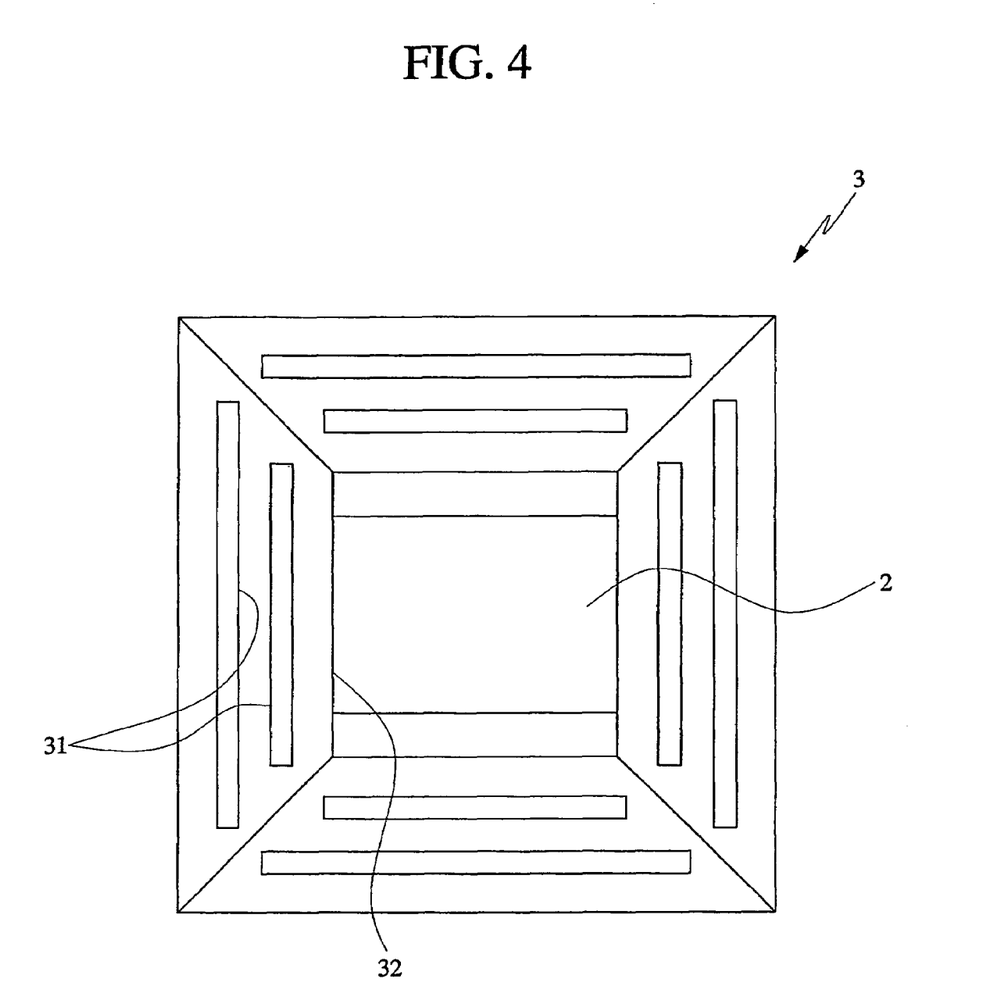
FIG. 4 is a plan view for illustrating an independent lighting unit in a vision inspection apparatus using total reflection mirrors in accordance with the present invention.

An independent lighting unit 3 is fixedly installed at a just upper part of the board position control module 2. The independent lighting unit 3, as shown in FIG. 4, is formed by arranging a primary lighting (an LED lighting or a halogen lighting 31) around a periphery of a visual passageway 32 passing through its center, and most closely installed to the board position control module 2. Therefore, the independent lighting unit 3 illuminates light to the printed circuit board (PCB) on the board position control module 2 (S2).

The photographing position control module 4 is located at a just upper part of the visual passageway 32 passed through the center of the dependent lighting unit 5. The photographing position control module 4 is provided with X-Y axis motors 41 and 42 of which total reflection mirrors 411 and 421 are attached on the axes, and the X-Y axis motors 41 and 42 rotate the total reflection mirrors 411 and 412 attached to the axes to vary an incidence angle to change photographing position coordinates. The total reflection mirrors 411 and 421 attached on the axes of the X-Y axis motors 41 and 42 apply to a silver coated mirror for completely reflecting light entered from the printed circuit board to reflect images of the printed circuit board (S3).

A camera 6 for obtaining images of the inspection area is installed on the same horizontal line of the total reflection mirror 411 attached to the X-axis motor, and the camera 6 is connected to a control unit 7 including a motion controller 71, a lighting controller 72 and an image processor 73, and a vision processing unit 8 for reading the images.

At this time, the motion controller 71 of the control unit 7 apply to a motor controller to control a motor and an output means included in the photographing position control module 4 and the board position control module 2 and to monitor overall input/output devices of the vision inspection apparatus 1 of the present invention, and the lighting controller 72 adopts an I/O board (one-chip micro-controller) and a peripheral circuit to adjust an on-off control and a luminous intensity of the independent lighting unit 3.

In addition, the image processor 73 apply to an image grabber to adjust the camera 6 and to photograph the image periodically or non-periodically when the image of an inspection object is entered to the camera 6 through the photographing position control module 4, and converts the image into digital data so that the digital data are processed in the system processor depending upon a use (S4).

Figure 5:
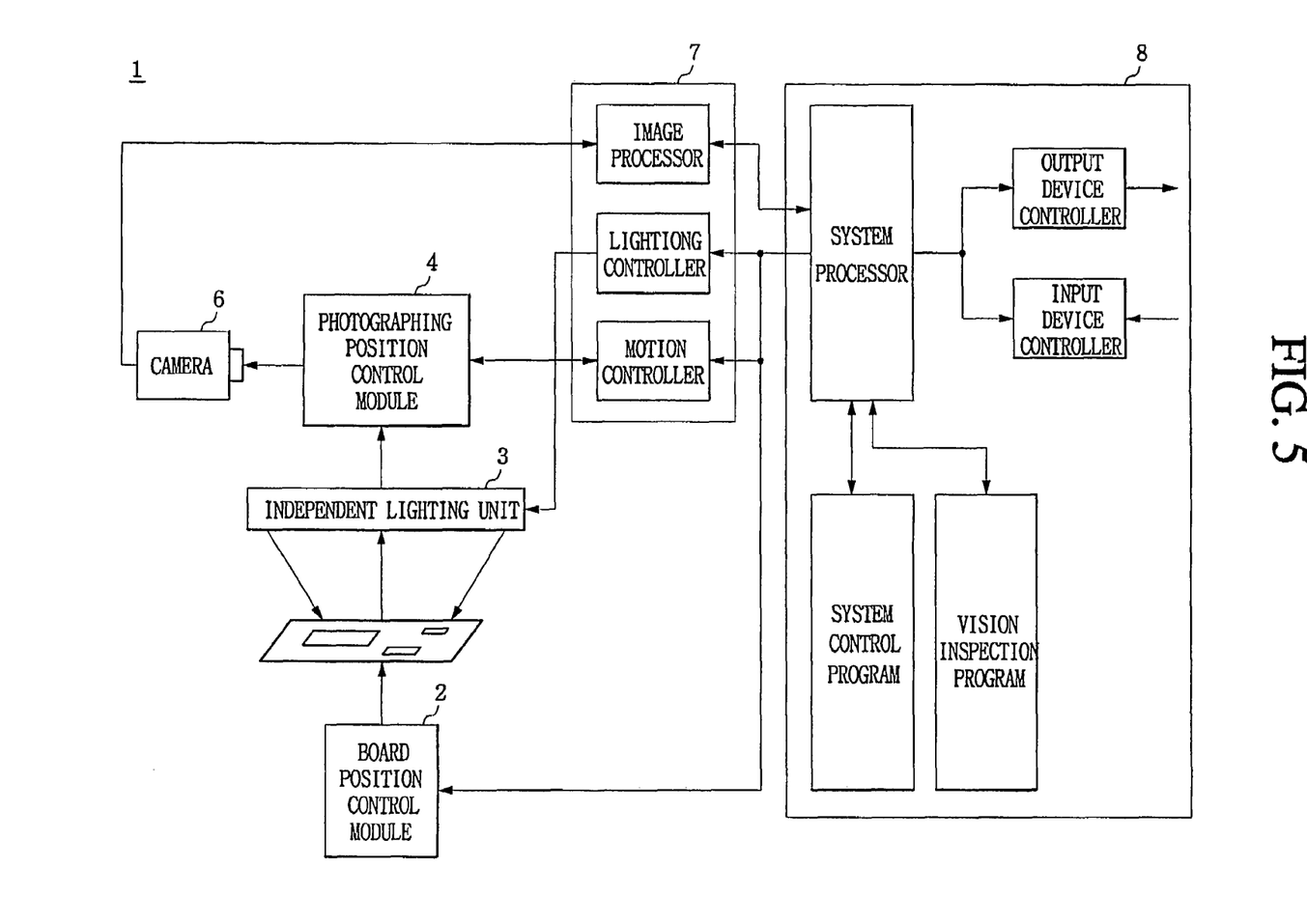
FIG. 5 is a conceptual view for illustrating a vision inspection apparatus using total reflection mirrors in accordance with the present invention.

As shown in FIG. 5, the motion controller 71, the lighting controller 72 and the image processor 73 composing the control unit 7 are electrically connected to the vision processing unit 8 to be operated by a control signal of the vision processing unit 8.

The vision processing unit 8 accomplishes physical controls such as a photographing position control, a processing of the photographed image, a lighting control and a board position control as well as an inspection operation and a data calculating operation depending upon a system control program, and includes an output device controller for outputting operation contents and tested results to a monitor and an input device controller for inputting various matters by an operator to read the image obtained by the camera to judge whether the mounted components are good or bad (S5).

Figure 6:
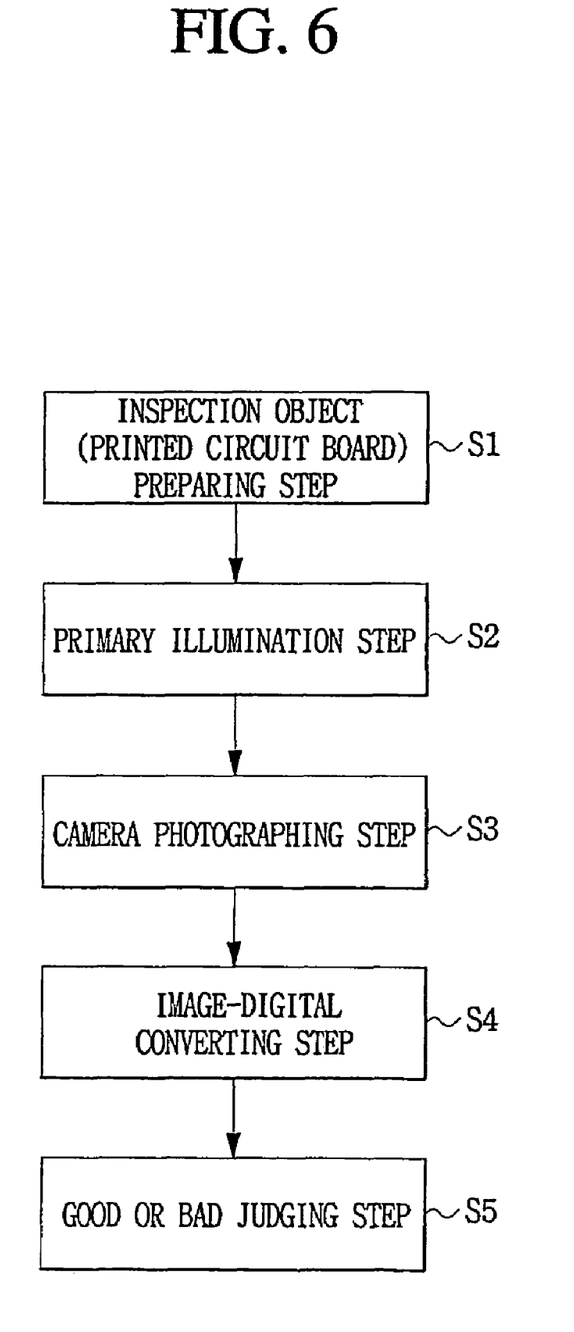
FIG. 6 is a flow chart for illustrating a vision inspection method using total reflection mirrors in accordance with the present invention.

Therefore, when the photographing and the inspection are completed as the inspection positions are moved on the printed circuit board sequentially, the conveyor of the board position control module 2 is operated to move the printed circuit board to an apparatus in a process after the inspection, repeating the vision inspection method as described above, the inspection operation of the printed circuit board is accomplished successively.

The vision inspection apparatus 1 and the vision inspection method of the present invention is capable of remarkably decreasing a volume of the apparatus itself in comparison with the prior art method of moving the camera or the printed circuit board adopted in a surface mounting assembly line having many spatial restrictions since the photographing position is changed by rotating the total reflection mirrors 411 and 421 of the photographing position control module 4 in the fixed state of the camera 6 and the printed circuit board, minimizing a driving torque and a vibration on moving and stopping as the total reflection mirrors 411 and 421 only are rotated, accomplishing a high speed inspection since a moving operation between the photographing positions is promptly achieved as a rotating number of the motor for moving the same distance in the printed circuit board is relatively small, and remarkably reducing inferior goods due to the vibration since there is little vibrations added to the inspection objects during the inspection.

Figure 3B:
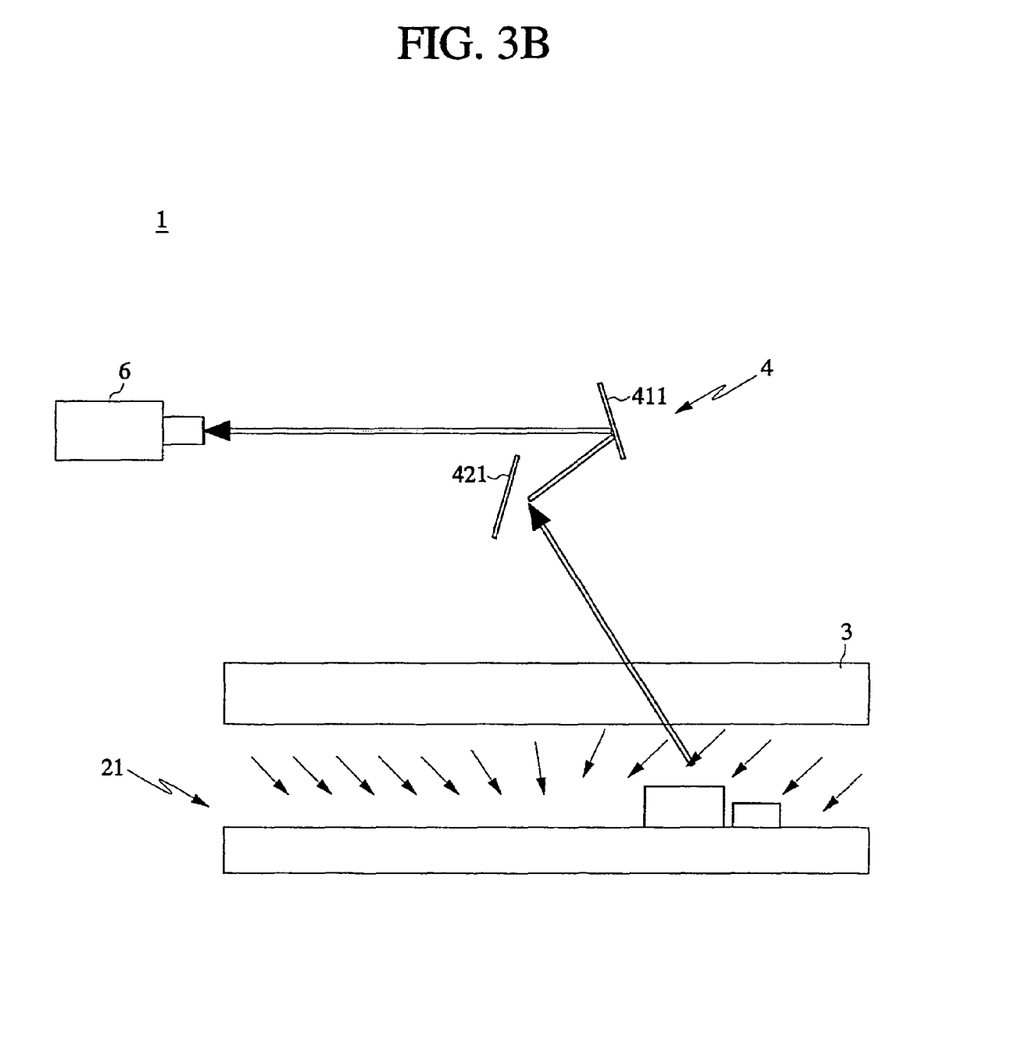
FIG. 3B is a structural view for illustrating an image obtaining operation of a vision inspection apparatus using total reflection mirrors in accordance with the present invention.

Especially, as shown in FIG. 3B, a stationary direct illuminating method is embodied through the independent lighting unit 3 mostly closely installed to the printed circuit board to minimize a quantity reduction of light of a light source and a quantity reduction of light of an image generated as passed through a half mirror like the prior art, and to improve a quantity reduction of light generated due to a long distance of the illumination source and the inspection object, thereby improving reliability of the inspection through distinctly image obtainment.

In addition, there is an advantage of preventing shadows of different sizes of components mounted on the printed circuit board from generating by illuminating light through the independent lighting unit 3 at all directions of an upper part of the printed circuit board.

Figure 7A:
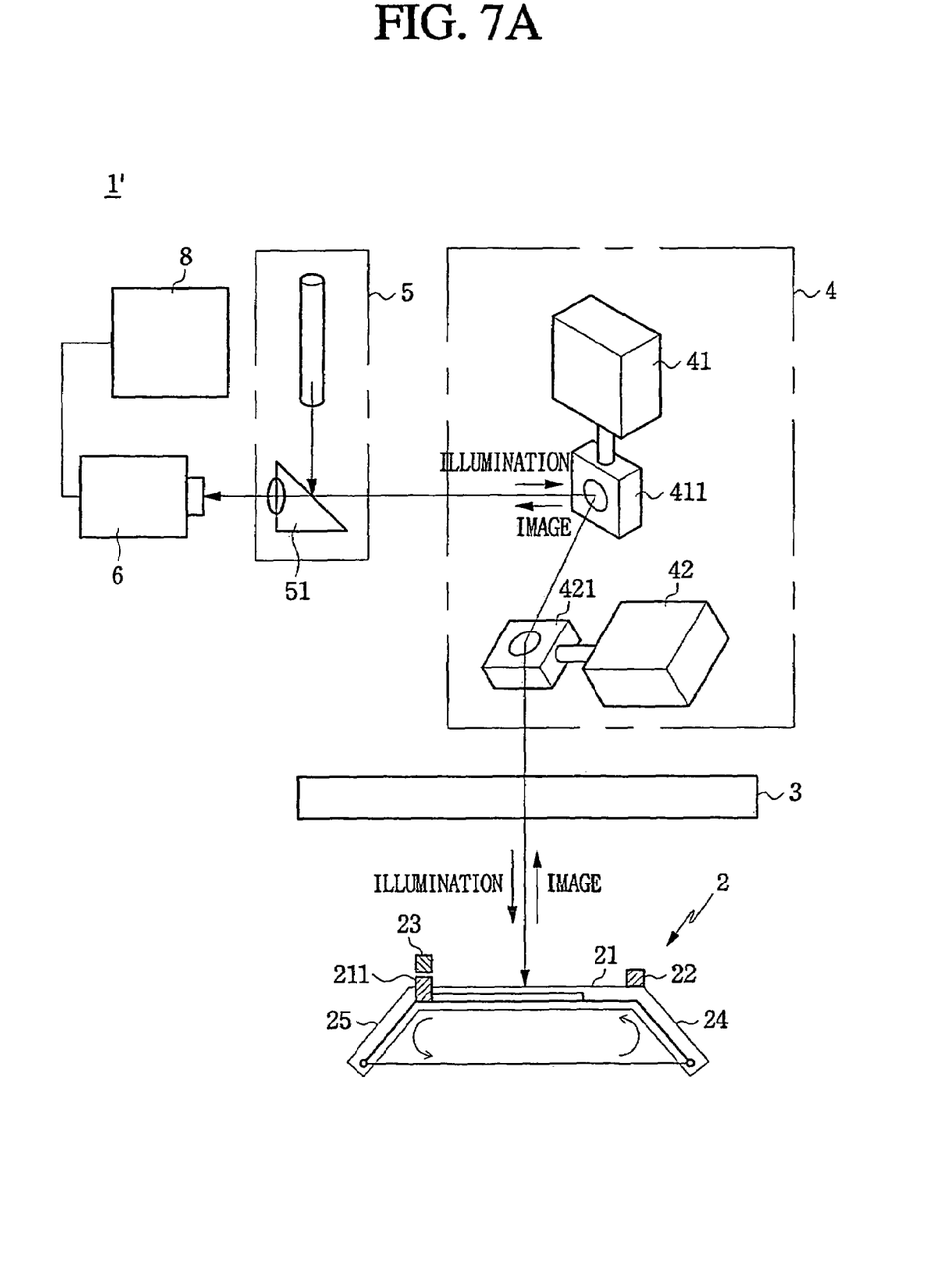
FIG. 7A is an overall structural view for illustrating another embodiment of a vision inspection apparatus using total reflection mirrors in accordance with the present invention.

Referring to FIGS. 7A to 9, in another embodiment of a vision inspection apparatus 1' and a vision inspection method in accordance with the present invention, a dependent lighting unit 5 is installed between the camera 7 and the photographing position control module 4. The dependent lighting unit 5 illuminates the printed circuit board through a secondary illumination light (a laser illumination light or a halogen illumination light), and, as shown in FIG. 7A, is provided with a half reflection mirror (a prism or a half coated mirror 51) for penetrating a part of light and reflecting a part of the light to enter the light illuminated by the secondary illumination light 52 into the total reflection mirror 411 attached to the X-axis motor 41 of the photographing position control module 4 located at a horizontal line (S2').

Figure 8:
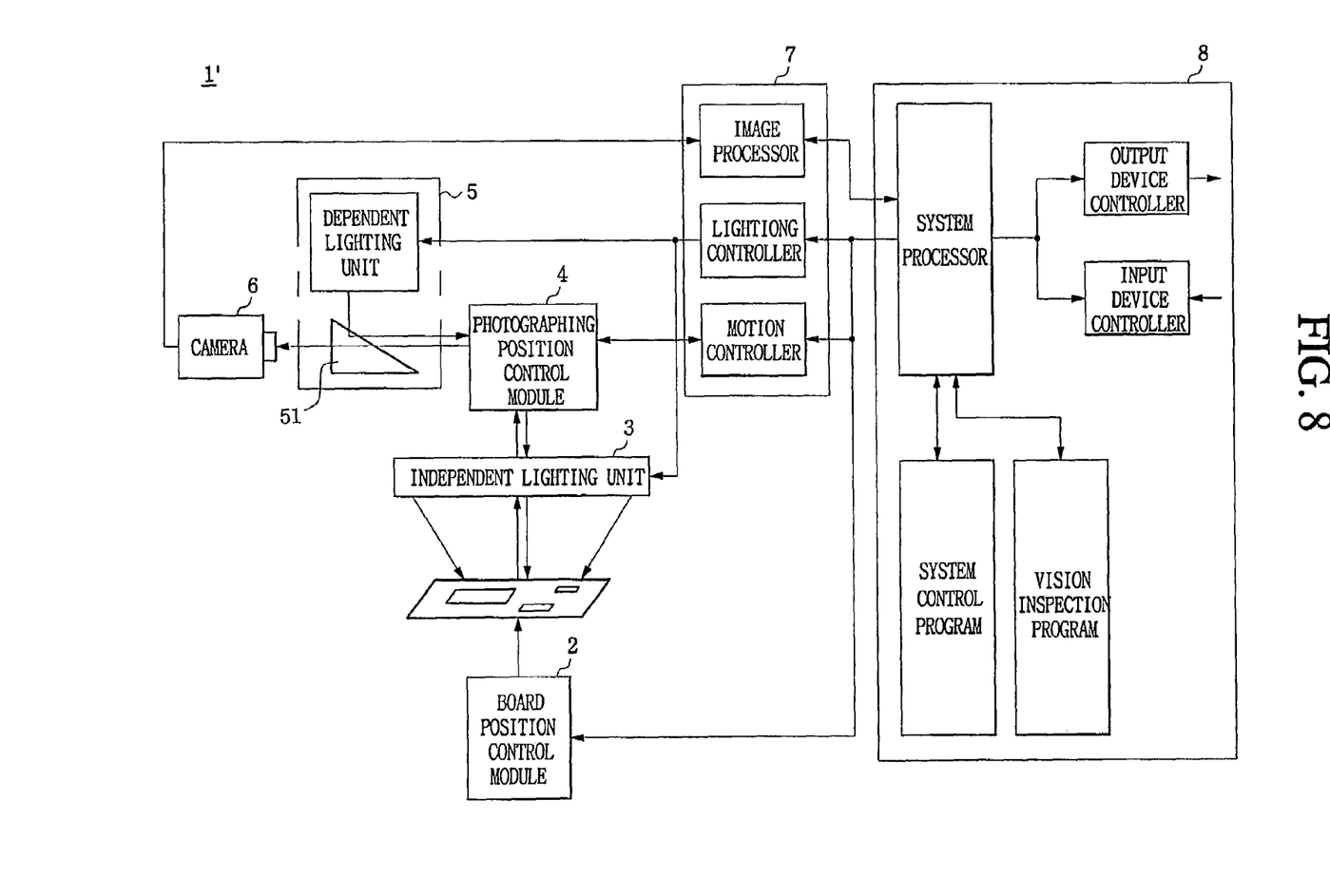
FIG. 8 is a conceptual view for illustrating another embodiment of a vision inspection apparatus using total reflection mirrors in accordance with the present invention.
Figure 9:
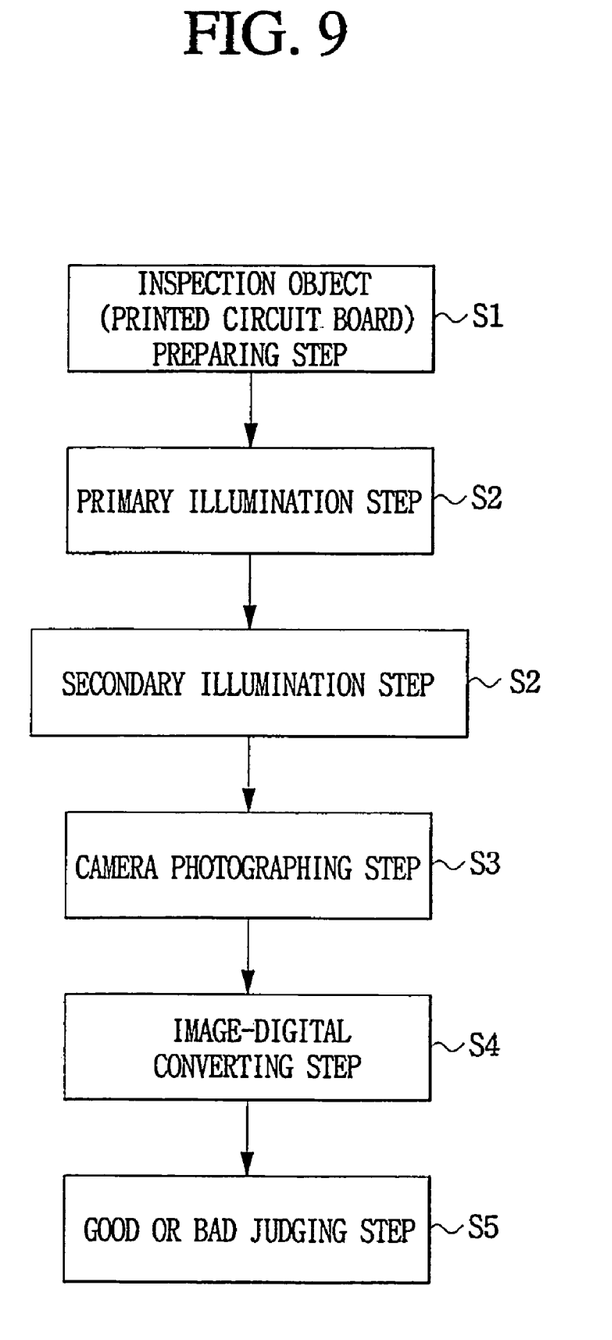
FIG. 9 is a flow chart for illustrating another embodiment of a vision inspection method using total reflection mirrors in accordance with the present invention.

At this time, the dependent lighting unit 5, as shown in FIG. 8, is connected to the illumination controller 72 to adjust an on/off control and luminous intensity.

In addition, the photographing position control module 4 rotates the total reflection mirrors 411 and 421 attached to the axes of the X-Y axis motors 41 and 42 to vary an incidence angle of the light illuminated from the dependent lighting unit 5, thereby accomplishing a function of changing illumination location coordinates, and a function of changing photographing location coordinates by varying also a reflection angle.

Figure 7B:
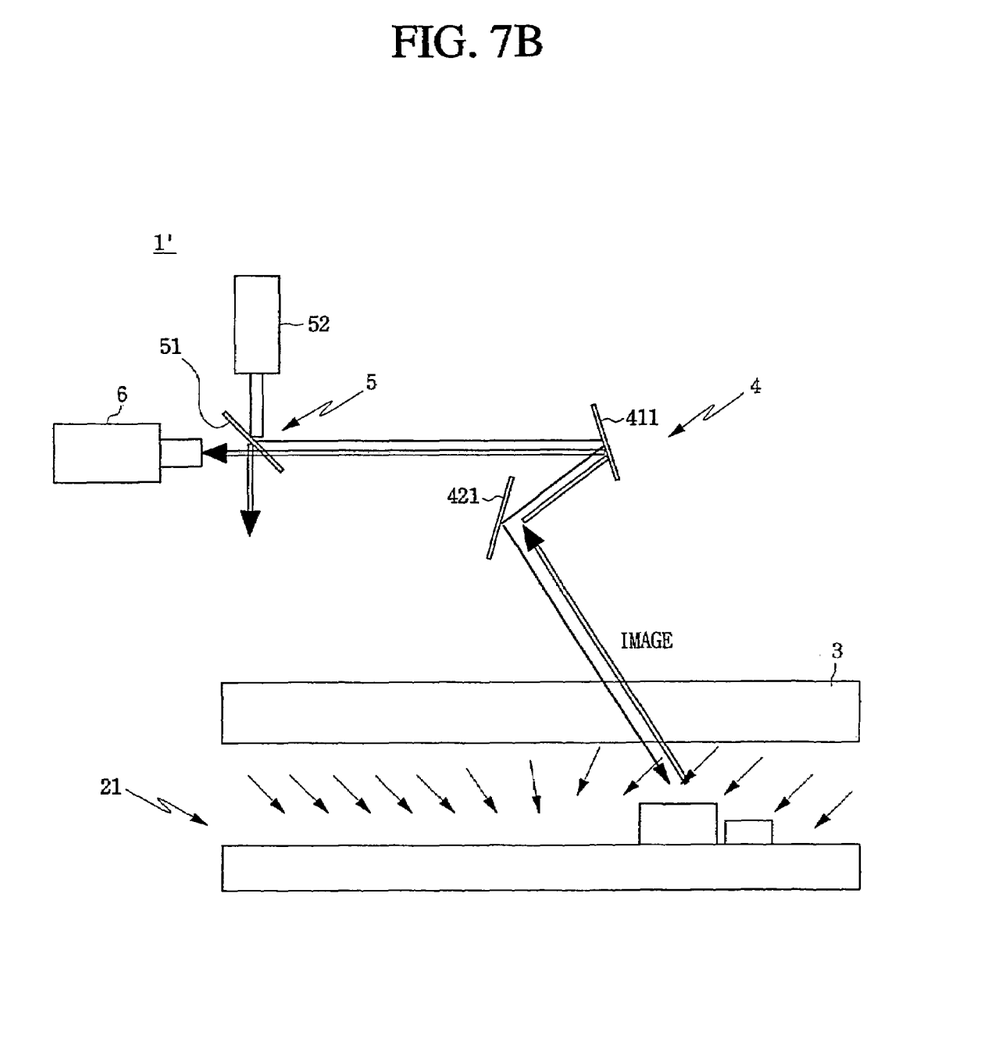
FIG. 7B is a structural view for illustrating an image obtaining operation of another embodiment of a vision inspection apparatus using total reflection mirrors in accordance with the present invention.

Therefore, another embodiment of the present invention, as shown in FIG. 7B, can obtain images in a state primarily and secondarily illuminated by the independent lighting unit 3 and the dependent lighting unit 5 on an inspection area of the printed circuit board. That is, when intense light is illuminated on a certain part of the inspection object to obtain a special image, it can be effectively used.

Then, the obtained image is repeatedly reflected through the total reflection mirrors 411 and 421 attached to the axes of the X-Y axis motors 41 and 42 to penetrate the half reflection mirror 51 to be transmitted to the camera 6.

INDUSTRIAL APPLICABILITY

As described above, a vision inspection apparatus and method using total reflection mirrors have effects of minimizing a driving torque and a vibration by changing a photographing position by rotating X-Y axis total reflection mirrors of a photographing position control module, and increasing test operation efficiency since a changing operation of the photographing position is promptly accomplished.

Especially, the present invention, provided with a stationary direct illuminating type of independent lighting unit, has an effect capable of obtaining a clear image of the inspection object by increasing a quantity of light entered into the camera, and accomplishing a precise inspection by employing a direct illuminating method to the inspection object to prevent shadows from generating on the vision inspection of objects on which different sizes of components are mounted such as a printed circuit board.

While this invention has been described in connection with what is presently considered to be the most practical and preferred embodiment, it is to be understood that the invention is not limited to the disclosed embodiment, but on the contrary, it is intended to cover various modification within the spirit and the scope of the appended claims.

What is claimed is:

1. A vision inspection apparatus using total reflection mirrors comprising:
    a board position control module for fixing a printed circuit board on a suitable inspection position;
    an independent lighting unit installed at a just upper part of the board position control module and provided with a primary lighting for primarily illuminating the printed circuit board;
    a photographing position control module, installed at a just upper part of the dependent lighting unit, for changing an incidence angle and a reflection angle by attaching the total reflection mirrors on axes of X-Y axis motors for performing a photographing and an illumination on required location coordinates;
    a dependent lighting unit provided with a half reflection mirror for changing an illuminating position on the printed circuit board depending upon the photographing position as the photographing position control module is moved, reflecting light illuminated from a secondary lighting to the photographing position control module, and penetrating an image of the printed circuit board;
    a camera for obtaining images of the printed circuit board penetrated from the half reflection mirror;
    a control unit including a motion controller for controlling the photographing position control module and the board position control module, a lighting controller for controlling an operation of the independent lighting unit, and an image processor for controlling an operation of the camera and converting the image entered to the camera into digital data; and
    a vision processing unit for reading the image obtained through the camera and judging whether the image is good or bad.

2. The vision inspection apparatus using total reflection mirrors according to claim 1, wherein the board position control module is a conveyor structure including a board fixture provided with first and second detecting sensors for detecting a flow and a position of the printed circuit board and a stopper for forcefully stopping the printed circuit board by detected values.

3. The vision inspection apparatus using total reflection mirrors according to claim 1, wherein the board fixture forms inclined slopes at its one end and the other end to be located at a higher location than the conveyors of preceding/following apparatuses.

4. The vision inspection apparatus using total reflection mirrors according to claim 1, wherein the independent lighting unit arranges and installs a primary lighting around a periphery of a visual passageway passing through a center thereof to illuminate the printed circuit board at all directions.

5. The vision inspection apparatus using total reflection mirrors according to claim 1, wherein the independent lighting unit is closely installed at a just upper part of the board position control module.

6. A vision inspection method using total reflection mirrors, the method comprising the steps of:
    fixing a printed circuit board on a suitable inspection position with a board position control module;
    primarily illuminating the printed circuit board with an independent lighting unit;
    illuminating light of a secondary lighting reflected by a half reflection mirror of a dependent lighting unit on required location coordinates of the printed circuit board, and adjusting an incidence angle and a reflection angle with the total reflection mirrors attached on axes of X-Y axis motors in order to transmit an image of the printed circuit board to a camera;
    converting the image penetrated from the half reflection mirror of the dependent lighting unit and entered to the camera into digital data; and
    reading the image obtained through the camera and judging whether mounted components are good or bad.

* * * * *